(12) United States Patent
Kimberley et al.

(10) Patent No.: US 6,458,739 B1
(45) Date of Patent: Oct. 1, 2002

(54) POLYMERIZATION CATALYSTS

(75) Inventors: Brian Stephen Kimberley, Surrey; John Norman Reid Samson, Stirling, both of (GB)

(73) Assignee: BP Chemicals Limited, London (GB)

( * ) Notice: Subject to any disclaimer, the term of this patent is extended or adjusted under 35 U.S.C. 154(b) by 35 days.

(21) Appl. No.: 09/659,582

(22) Filed: Sep. 11, 2000

Related U.S. Application Data

(63) Continuation of application No. PCT/GB99/00715, filed on Mar. 10, 1999.

(30) Foreign Application Priority Data

| | | | |
|---|---|---|---|
| Mar. 12, 1998 | (GB) | ............................................. | 9805336 |
| Mar. 20, 1998 | (GB) | ............................................. | 9806106 |
| Mar. 27, 1998 | (GB) | ............................................. | 9806661 |
| May 7, 1998 | (GB) | ............................................. | 9809598 |
| Jul. 3, 1998 | (GB) | ............................................. | 9814496 |
| Sep. 24, 1998 | (GB) | ............................................. | 9820700 |

(51) Int. Cl.$^7$ .............................. B01J 31/18; C08F 4/44
(52) U.S. Cl. ........................ 502/155; 502/104; 502/167; 526/64; 526/154; 526/161; 526/171; 526/172; 526/352; 526/901
(58) Field of Search .......................... 526/172, 64, 352, 526/161, 154, 901, 171; 502/104, 117, 155, 167, 154

(56) References Cited

U.S. PATENT DOCUMENTS 5,955,555 A * 9/1999 Bennett ...................... 526/133

OTHER PUBLICATIONS

G.J.P. Britovsek et al., "Novel Olefin Polymerization Catalysts Based on Iron and Cobalt", Chem. Commun., No. 7, pp. 849–850, (1998).
C. Pellecchia et al., "Isotactic–Specific Polymerization of Propene with an Iron–Based Catalyst: Polymer End Groups and Regiochemistry of Propagation", Macromol. Rapid Commun. vol. 19, No. 19, pp. 651–655.

* cited by examiner

Primary Examiner—David W. Wu
Assistant Examiner—R. Harlan
(74) Attorney, Agent, or Firm—Finnegan, Henderson, Farabow, Garrett and Dunner, L.L.P.

(57) ABSTRACT

The present invention relates to transition metal compounds and to polymerization catalyst systems employing said transition metal compounds.

31 Claims, No Drawings

POLYMERIZATION CATALYSTS

This application is a continuation of international application No. PCT/GB99/00715 filed Mar. 10, 1999.

The present invention relates to transition metal compounds and to polymerisation catalyst systems employing them.

The use of certain transition metal compounds to polymerise 1-olefins, for example, ethylene, is well established in the prior art. The use of Ziegler-Natta catalysts, for example, those catalysts produced by activating titanium halides with organometalric compounds such as triethylaluminium, is fundamental to many commercial processes for manufacturing polyolefins. Over the last twenty or thirty years, advances in the technology have led to the development of Ziegler-Natta catalysts which have such high activities that that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

Commodity polyethylenes are commercially produced in a variety of different types and grades. Homopolymerisation of ethylene with transition metal based catalysts leads to the production of so-called "high density" grades of polyethylene. These polymers have relatively high stiffness and are useful for making articles where inherent rigidity is required. Copolymerisation of ethylene with higher 1-olefins (eg butene, hexene or octene) is employed commercially to provide a wide variety of copolymers differing in density and in other important physical properties. Particularly important copolymers made by copolymerising ethylene with higher 1-olefins using transition metal based catalysts are the copolymers having a density in the range of 0.91 to 0.93. These copolymers which are generally referred to in the art as "linear low density polyethylene" are in many respects similar to the so called "low density" polyethylene produced by the high pressure free radical catalysed polyrnerisation of ethylene. Such polymers and copolymers are used extensively in the manufacture of flexible blown film.

An important feature of the microstructure of the copolymers of ethylene and higher 1-olefins is the manner in which polymerised comonomer units are distributed along the "backbone" chain of polymerised ethylene units. The conventional Ziegler-Natta catalysts have tended to produce copolymers wherein the polymerised comonomer units are clumped together along the chain. To achieve especially desirable film properties from such copolymers the comonomer units in each copolymer molecule are preferably not clumped together, but are well spaced along the length of each linear polyethylene chain. In recent years the use of certain metallocene catalysts (for example biscyclopentadienyizirconium dichloride activated with alumoxane) has provided catalysts with potentially high activity and capable of providing an improved distribution of the comonomer units. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

WO98/27124 discloses that ethylene may be polymerised by contacting it with certain iron or cobalt complexes of selected 2,6-pyridinecarboxaldehydebis(imines) and 2,6-diacylpyridinebis(imines). These complexes are disclosed as being suitable for preparing homopolymers of ethylene. Activities of from 6 to 2985 g/mmol/h/bar are shown.

We have developed novel catalysts utilising complexes such as those disclosed in WO 98/27124 which provide excellent activities and products. Accordingly in a first aspect the invention provides a catalyst for the polymerisation of olefins comprising (1) a compound of the formula B

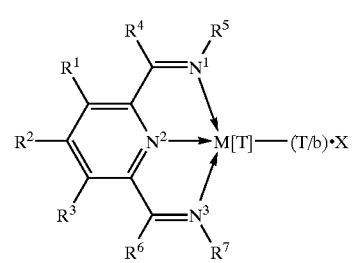

Formula B wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents;

(2) an activator which is an alkylalumoxane; and
(3) additionally to (2), a compound of the formula $AlR_3$, where each R is independently $C_1$–$C_{12}$ alkyl or halo.

We have found that the incorporation of component (3) into the catalyst can result in significant improvements in activity. The three substituents R in compound (3), which may be the same or different, are preferably hydrogen, methyl, ethyl, butyl or chloro. Preferred compounds (3)

include trimethylaluminium (TMA), triethylaluminium (TEA), tri-isobutylaluminium (TIBA), tri-n-octylaluminium, ethylalumninium dichloride and diethylaluminium chloride. Most preferred are TMA and TIBA However the preferred compound (3) may depend on the polymerisation conditions in which the catalyst is employed: for example, TMA is particularly effective at improving catalyst activity in gas phase and also the activity of unsupported catalysts in slurry phase, whilst TIBA is particularly effective in slurry phase polymerisation generally.

As activator (2), the catalyst of the invention includes an alkylalumoxane which is normally a $(C_1-C_4)$ alkylalumoxane, the alkyl group generally being methyl, ethyl, propyl or isobutyl. Preferred is methylalumoxane (also known as methylaluminoxane or MAO) or modified methylalumoxane (MMAO), which additionally contains isobutylalumoxane. The term "alkylalumoxane" as used in this specification includes alkylalumoxanes available commercially which may contain a proportion, typically about 10 wt %, but optionally up to 50 wt %, of the corresponding trialkylaluminium; for instance, commercial MAO usually contains approximately 10 wt % trimethylaluminium (TMA), whilst commercial MMAO contains both TMA and TIBA. Quantities of alkylalumoxane quoted herein include such trialkylalkylaluminium impurities, and accordingly component (3) in this invention is considered to comprise compounds of the formula $AlR_3$ additional to any $AlR_3$ compound incorporated within the alkylalumoxane (2), and quantities of component (3) quoted herein are calculated on that basis.

In the preparation of the catalyst systems of the present invention the quantity of activating compound (2) to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium per Fe, Co, Mn or Ru metal atom in the compound of Formula B. The amount of activator (2) required for optimum performance may also depend on the amount of alkylaluminium compound (3) present. For example, when compound (3) is trimethyl aluminium (TMA), and the amount of TMA in the catalyst is less than 500 molar equivalents relative to the metal atom of compound (1), the amount of alkylalumoxane (usually MAO) is preferably at least 1000 molar equivalents. However if 500 equivalents or more of TMA are present, the optimum amount of alkylalumoxane (usually MAO) is from 500 to 1000 equivalents.

Preferably in Formula B above M is Fe[II], Fe[III], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents.

Further compounds for use in the present invention include those comprising the skeletal unit depicted in Formula Z:

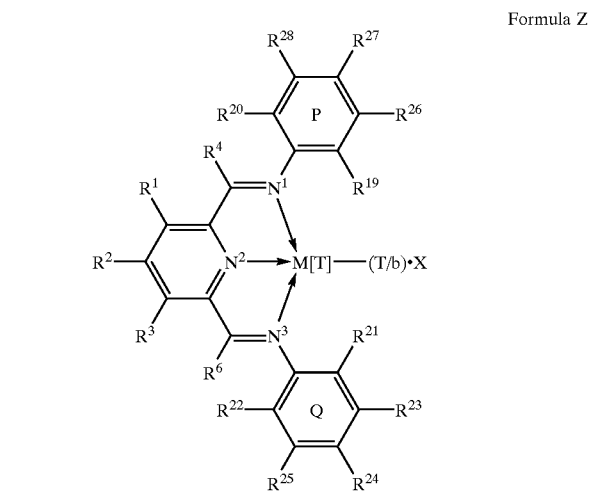

Formula Z wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system. In this particular aspect of the present invention, in the case that neither of the ring systems P and Q forms part of a polyaromatic ring system, it is preferred that at least one of $R^{19}$ and $R^{20}$, and at least one of $R^{21}$ and $R^{22}$ is selected from hydrocarbyl, substituted hydrocarbyl, heterohydrocarbyl or substituted heterohydrocarbyl, and most preferably each of $R^{19}$, $R^{20}$, $R^{21}$ and $R^{22}$ is selected from hydrocarbyl, substituted hydrocarbyl, heterohydrocarbyl or substituted heterohydrocarbyl.

Subject to the foregoing provisos regarding $R^{19}$, $R^{20}$, $R^{21}$ and $R^{22}$ in Formula Z, $R^1$ to $R^4$, $R^6$ and $R^{19}$ to $R^{28}$ in the compounds depicted in Formulae B and Z of the present invention are preferably independently selected from hydrogen and $C_1$ to $C_8$ hydrocarbyl, for example, methyl, ethyl, n-propyl, n-butyl, n-hexyl, and n-octyl. In Formula B, $R^5$ and $R^7$ are preferably independently selected from substituted or unsubstituted alicyclic, heterocyclic or aromatic groups, for example, phenyl, 1-naphthyl, 2-naphthyl, 2-methylphenyl, 2-ethylphenyl, 2,6-diisopropylphenyl, 2,3-diisopropylphenyl, 2,4-disopropylphenyl, 2,6-di-n-butylphenyl, 2,6-dimethylphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5-dichloro2,6-diethylphenyl, and 2,6,bis (2,6-dimethylphenyl)phenyl, cyclohexyl and pyridinyl.

The ring systems P and Q in Formula Z are preferably independently 2,6-hydrocarbylphenyl or fused-ring polyaromatic, for example, 1-naphthyl, 2-naphthyl, 1-phenanthrenyl and 8-quinolinyl.

In the compound of Formula B and Z of the present invention, M is preferably Fe[II] or Co[II].

Yet further compounds suitable for the catalyst systems of the present invention are those comprising the skeletal unit depicted in Formula T:

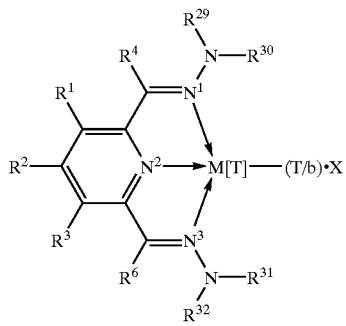

Formula T wherein M is Fe[II], Fe[III], Co[I], Co[II], Co[III], Mn[I], Mn[II], Mn[III], Mn[IV], Ru[II], Ru[III] or Ru[IV]; X represents an atom or group covalertly or ionically bonded to the transition metal M; T is the oxidation state of the transition metal M and b is the valency of the atom or group X; $R^1$ to $R^4$, $R^6$ and $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents.

In the compound of Formula B of the present invention, M is preferably Fe[II]. In the compounds of Formula Z or Formula T of the present invention, M is preferably Fe[II], Mn[II] or Co[II].

Examples of the atom or group X in the compounds of Formula B, Z and T are halide, for example, chloride, bromide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl. Chloride is particularly preferred.

The following are examples of nitrogen-containing transition metal complexes that can be employed in the catalyst of the present invention:

2,6-diacetylpyridinebis(2,6-diisopropylanil)FeCl$_2$
2,6-diacetylpyridine(2,6-diisopropylanil)MnCl$_2$2,6-
    diacetylpyridine(2,6-diisopropylanil)CoCl$_2$
2,6-diacetylpyridinebis(2-tert.-butylanil)FeCl$_2$
2,6-diacetylpyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,6-dimethylanil)FeCl$_2$
2,6-diacetylpyridinebis(2,4,6 trimethyl anil)FeCl$_2$
2,6-dialdiminepyridinebis(2,6-dimethylanil)FeCl$_2$
2,6-dialdiminepyridinebis(2,6-diethylanil)FeCl$_2$
2,6dialdiminepyridinebis(2,6-diisopropylanil)FeCl$_2$
2,6-dialdiminepyridinebis(1-naphthil)FeCl$_2$ and
2,6-bis(1,1-diphenylhydrazone)pyridine.FeCl$_2$.

A preferred complex of the present invention is 2,6-diacetylpyridinebis(2,4,6 trimethyl anil)FeCl$_2$.

In a further aspect of the present invention the catalyst system may additionally comprise (4) a neutral Lewis base. Neutral Lewis bases are well known in the art of Ziegler-Natta catalyst polymerisation technology. Examples of classes of neutral Lewis bases suitably employed in the present invention are unsaturated hydrocarbons, for example, alkenes or alkynes, primary, secondary and tertiary amines, amides, phosphoramides, phosphines, phosphites, ethers, thioethers, nitrites, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2) and (4) of the catalyst system can be brought together simultaneously or in any desired order. However, if components (2) and (4) are compounds which interact together strongly, for example, form a stable compound together, it is preferred to bring together either components (1) and (2) or components (1) and (4) in an initial step before introducing the final defined component. Preferably components (1) and (4) are contacted together before component (2) is introduced. The quantities of components (1) and (2) employed in the preparation of this catalyst system are suitably as described above in relation to the catalysts of the present invention. The quantity of the neutral Lewis Base [component (4)] is preferably such as to provide a ratio of component (1):component (4) in the range 100:1 to 1:1000, most preferably in the range 1:1 to 1:20. Components (1), (2) and (4) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures eg up to 120° C. can be carried out if desired, eg to achieve better mixing of the components. It is preferred to carry out the bringing together of components (1), (2) and (4) in an inert atmosphere (eg dry nitrogen) or in vacua. If it is desired to use the catalyst on a support material (see below), this can be achieved, for example, by preformiing the catalyst system comprising components (1), (2) and (4) and impregnating the support material preferably with a solution thereof, or by introducing to the support material one or more of the components simultaneously or sequentially. If desired the support material itself can have the properties of a neutral Lewis base and can be employed as, or in place of component (4). An example of a support material having neutral Lewis base properties is poly(aminostyrene) or a copolymer of styrene and aminostyrene (ie vinylaniline).

The compounds employed as catalysts in the catalyst systems of the present invention can if desired comprise more than one of the above-defined transition metal compounds. The catalyst may comprise, for example a mixture of 2,6-diacetylpyridinebis(2,6-diisopropylanil)FeCl$_2$ complex and 2,6-diacetylpyridinebis (2,4,6-trimethylanil)FeCl$_2$ complex, or a mixture of 2,6-diacetylpyridine(2,6-diisopropylanil)CoCl$_2$ and 2,6-diacetylpyridinebis(2,4,6-trimethylanil)FeCl$_2$. In addition to said one or more defined transition metal compounds, the catalysts can also include one or more other types of transition metal compounds or catalysts, for example, transition metal compounds of the type used in conventional Ziegler-Natta catalyst systems, metallocene-based catalysts, or heat activated supported chromium oxide catalysts (eg Phillips-type catalyst).

The catalysts employed in the present invention can be unsupported or supported on a support material, for example, silica, alumina, or zirconia, or on a polymer or prepolymer, for example polyethylene, polystyrene, or poly (aminostyrene). If desired the catalysts can be formed in situ in the presence of the support material, or the support material can be pre-impregnated or premixed, simultaneously or sequentially, with one or more of the catalyst components. The catalysts can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds with alumoxane in a suitable inert diluent, for example a volatile hydrocarbon, slurrying a particulate support material with the product and evaporating the volatile diluent. The quantity of support material employed can vary widely, for example from 100,000 to 1 grams per gram of metal present in the transition metal compound.

A further aspect of the invention comprises the use of a compound of the formula AlR$_3$, where each R is independently C$_1$–C$_{12}$ alkyl or halo, to enhance the catalytic activity in polymerisation of 1-olefins of a compound of the Formula B as defined above.

The present invention further provides a process for the polymerisation and copolymerisation of 1-olefins comprising contacting the monomeric olefin under polymerisation conditions with a polymerisation catalyst system comprising
(1) a compound of the formula B as defined above
(2) an alkylalumoxane activator
(3) additionally to (2), a compound of the formula AlR$_3$, where each R is independently C$_1$–C$_{12}$ alkyl or halo.

In a preferred process the catalyst compound (1) is activated with the alkylalumoxane (2) before contact with the monomer to be polymerised.

The polymerisation conditions can be, for example, solution phase, slurry phase or gas phase. If desired, the catalyst system can be used to polymerise ethylene under high pressure/high temperature process conditions wherein the polymeric material forms as a melt in supercritical ethylene. Preferably the polymerisation is conducted under gas phase fluidised bed conditions. Slurry phase polymerisation conditions or gas phase polymerisation conditions are particularly useful for the production of high density grades of polyethylene. In these processes the polymerisation conditions can be batch, continuous or semi-continuous. In the slurry phase process and the gas phase process, the catalyst is generally fed to the polymerisation zone in the form of a particulate solid. This solid can be, for example, an undiluted solid catalyst system formed from a nitrogen-containing complex and an activator, or can be the solid complex alone. In the latter situation, the activator can be fed to the polymerisation zone, for example as a solution, separately from or together with the solid complex. Preferably the catalyst system or the transition metal complex component of the catalyst system employed in the slurry polymerisation and gas phase polymeriastion is supported on a support material. Most preferably the catalyst system is supported on a support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques.

In the slurry phase polymerisation process the solid particles of catalyst, or supported catalyst, are fed to a polymerisation zone either as dry powder or as a slurry in the polymerisation diluent. Preferably the particles are fed to a polymerisation zone as a suspension in the polymerisation diluent. The polymerisation zone can be, for example, an autoclave or similar reaction vessel, or a continuous loop reactor, e.g. of the type well-known in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of nitrogen-containing transition metal complex employed in the catalyst system). This means that relatively very small quantities of transition metal complex are consumed in commercial processes using the process of the present invention. It also means that when the polymerisation process of the present invention is operated under polymer recovery conditions that do not employ a catalyst separation step, thus leaving the catalyst, or residues thereof, in the polymer (eg as occurs in most commercial slurry and gas phase polymerisation processes), the amount of transition metal complex in the produced polymer can be very small. Experiments carried out with the catalyst of the present invention show that, for example, polymerisation of ethylene under slurry polymerisation conditions can provide a particulate polyethylene product containing catalyst so diluted by the produced polyethylene that the concentration of transition metal therein falls to, for example, 1 ppm or less wherein "ppm" is defined as parts by weight of transition metal per million parts by weight of polymer. Thus polyethylene produced within a polymerisation reactor by the process of the present invention may contain catalyst diluted with the polyethylene to such an extent that the transition metal content thereof is, for example, in the range of 1–0.0001 ppm, preferably 1–0.001 ppm. Using a catalyst comprising a nitrogen-containing Fe complex in accordance with the present invention in, for example, a slurry polymerisation, it is possible to obtain polyethylene powder wherein the Fe concentration is, for example, 1.03 to 0.11 parts by weight of Fe per million parts by weight of polyethylene.

Suitable monomers for use in the polymerisation process of the present invention are, for example, ethylene, propylene, butene, hexene, methyl methacrylate, methyl acrylate, butyl acrylate, acrylonitrile, vinyl acetate, and styrene. Preferred monomers for homopolymerisation processes are ethylene and propylene. The catalyst can also be used for copolymerising ethylene with other 1-olefins such as propylene, 1-butene, 1-hexene, 4-methylpentene-1, and octene.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid is small in relation to the quantity of polymer present in the polymerisation zone. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

In the preferred embodiment of the gas phase polymerisation process of the present invention, the gas phase polymerisation conditions are preferably gas phase fluidised bed polymerisation conditions.

Methods for operating gas phase fluidised bed processes for making polyethylene and ethylene copolymers are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (eg nitrogen) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, although it may be operated at pressures from 10 to 100 bars; and at temperatures for example, between 50 and 120 ° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (ie, the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and sprayed back into the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

The present invention is illustrated in the following Examples.

EXAMPLES

Example 1 shows the preparation of a novel iron compound (see Formula D below), and Example 3 shows the preparation of a novel cobalt compound (see Formula K), each compound being in accordance with the present invention.

In the Examples all manipulations of air/moisture-sensitive materials were performed on a conventional vacuum/inert atmosphere (nitrogen) line using standard Schlenk line techniques, or in an inert atmosphere glove box.

Example 1

Intermediate A [2,6-diacetylpyridinebis(2,6-diisopropylanil)] was prepared by the reaction of Intermediate B [2,6-diacetylpyridine] and Intermediate C [2,6-diisopropylaniline]. Intermediate A was then reacted with ferrous chloride in butanol to provide the compound of Formula D.

Preparation of Intermediate A

Using a procedure based on a related preparation (E. C. Alyea and P. H. Merrell, *Synth. React. Inorg. Metal-Org. Chem.*, 1974, 4, 535):—2,6-diisopropylaniline (3.46 ml, 18.4 mmol) was added dropwise to a solution of 2,6-diacetylpyridine (1.50 g, 9.2 mmol) in absolute ethanol (25 ml) [2,6-diisopropylaniline and 2,6-diacetylpyridine were obtained from Aldrich the former of which was freshly distilled before use]. A few drops of glacial acetic acid was added and the solution was refluxed for 48 h. Concentration of the solution to half volume and cooling to −78° C. gave intermediate A as pale yellow crystals (80%). Calcd for $C_{33}H_{43}N_3$: C, 82.3; H, 8.9; N, 8.7; Found: C, 81.9; H, 8.5; 8.7%. FABMS: M+ (481). $^1$H NMR (CDCl$_3$): 8.6–7.9[m, 3H, $C_5H_3N$], 7.2–6.9[m, 6H, $C_6(CHMe_2)H_3$], 2.73[sept, 4H, $CHMe_2$], 2.26[s, 6H, $C_5H_3N(CMeNAr)_2$] and 1.16[m, 24H, $CHMe_2$]. FABMS is fast atom bombardment mass spectrometry.

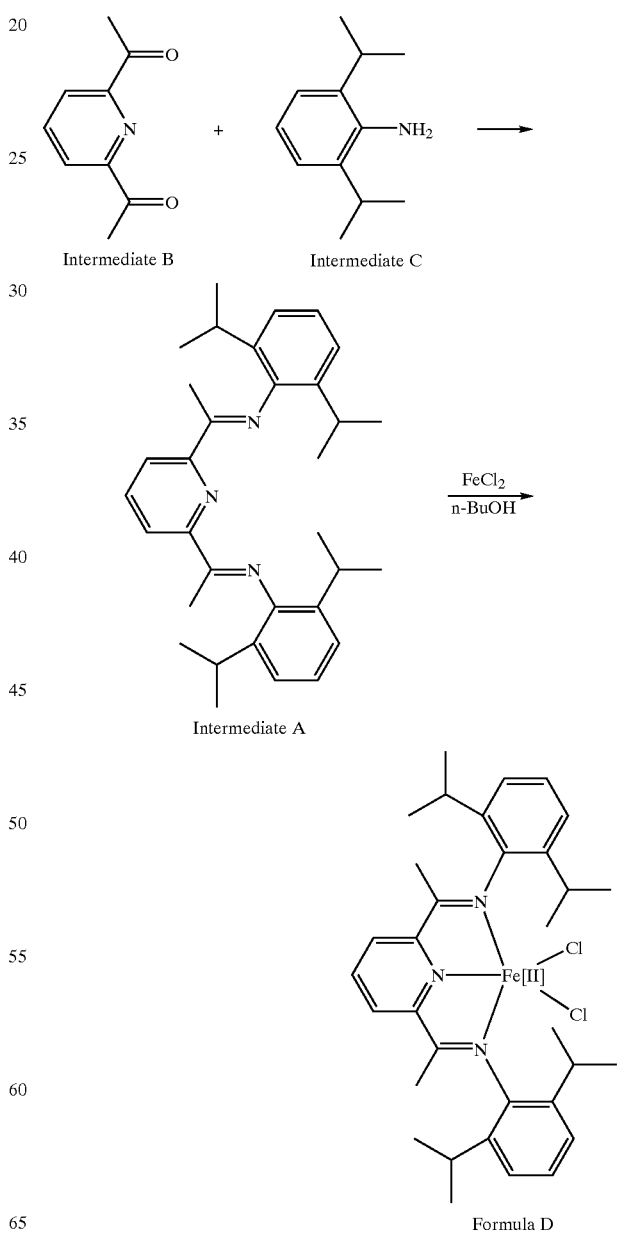

Intermediate B

Intermediate C

Intermediate A

Formula D

Preparation of the Formula D Compound

[2,6-diacetylpyridinebis(2,6-diisopropylanil)FeCl$_2$]

FeCl$_2$ (0.24 g; 1.89 mmol) was dissolved in hot n-butanol (20 ml) at 80° C. A suspension of 2,6-diacetylpyridinebis (2,6-diisopropylanil) (0.92 g; 1.89 mmol) in n-butanol was added dropwise at 80° C. The reaction mixture turned blue. After stirring at 80° C. for 15 minutes the reaction was allowed to cool down to room temperature. The reaction volume was reduced to a few ml, and petroleum ether (40/60) was added to precipitate the product (a blue powder), which was subsequently washed three times with 10 ml petroleum ether (40/60). The yield was 0.93 g (81%).

Mass spectrum: m/z 607 [M]+, 572 [M–Cl]+, 482 [M–FeCl$_2$]+.

Analysis—Calculated: for C$_{33}$H$_{43}$N$_3$FeCl$_2$: C, 65.14; H, 7.12; N, 6.91. Found: C, 64.19; H, 6.90; N, 6.70.

Example 3

Preparation of 2,6-diacetylpyridine(2,6-diisopropylanil)CoCl$_2$—Formula K

Cobalt chloride (CoCl$_2$—0.057 g; 0.44 mmol) was dissolved in hot n-butanol (10 ml) at 80° C. A suspension of Intermediate A [2,6-diacetylpyridinebis(2,6-diisopropylanil)] (0.21 g; 0.44 mmol) in n-butanol was added dropwise at 80° C. After stirring at 80° C. for 15 minutes the produced reaction mixture was allowed to cool to room temperature. The reaction volume was reduced to a few ml and petroleum ether (40/60) was added to precipitate the product. The olive green powdery precipitate was washed three times with 10 ml aliquots of petroleum ether (40/60). The yield of the cobalt complex (Formula K—see below) was 0.18 g (67% of theory). The mass spectrum showed m/z 575 [M–Cl]+, 538 [M–2Cl]+.

FORMULA K

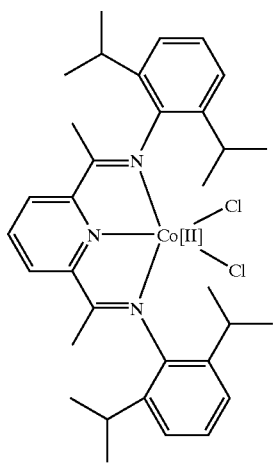

Examples 7 to 9

Preparation of Iron Complexes

Example 7

7.1—Preparation of 2,6-diacetylpyridinebis(2,4-dimethylanil)

The procedure was as for Example 4.1 except that 2,4-dimethyl aniline was used instead of 2-tertiarybutylaniline. The yield was 75% of theoretical.

$^1$H NMR(CDCl$_3$): 8.41, 7.90, 7.05, 6.90, 6.55, (m, 9H, ArH, pyrH), 2.36 (m, 6H, N=CCH$_3$, 6H, CCH$_3$), 2.13 (s, 6H, CCH$_3$).

Mass spectrum: m/z 369 [M]+.

7.2—Preparation of 2,6-diacetylpyridinebis(2,4-dimethylanil)FeCl$_2$

The procedure was as for Example 4.2 except that 2,6diacetylpyridinebis(2,4-dimethylanil) was employed instead of 2,6-diacetylpyridinebis(2-tert.-butylanil). The yield was 75% of theoretical.

Mass spectrum: m/z 496 [M]+, 461 [M–Cl]+, 425 [M–Cl$_2$]+.

Example 8

8.1 Preparation of 2,6-diacetylpyridinebis(2,6-dimethylanil)

The procedure was as for Example 4.1 except that 2,6-dimethyl aniline was used instead of 2-tertiarybutylaniline. The yield was 78% of theoretical.

$^1$H NMR(CDCl$_3$): 8.48, 8.13, 7.98, 7.08, 6.65, (m, 9H, ArH, pyrH), 2.25(s, 6H, N=CCH$_3$), 2.05 (m, 12H, CCH$_3$).

Mass spectrum: m/z 369 [M]+.

8.2—Preparation of 2,6-diacetylpyridinebis(2,6-dimethylanil)FeCl$_2$

The procedure was as for Example 4.2 except that 2,6-diacetylpyridinebis(2,6-dimethylanil) was employed instead of 2,6-diacetylpyridinebis(2-tert.-butylanil). The yield was 78% of theoretical.

Mass spectrum: m/z 496 [M]+, 461 [M–Cl]+, 425 [M–Cl$_2$]+.

Example 9

9.1 Preparation of 2,6-diacetylpyridinebis(2,4,6-trimethylanil)

The procedure was as for Example 4.1 except that 2,4,6-trimethyl aniline was used instead of 2-tertiarybutylaniline. The yield was 60% of theoretical.

$^1$H NMR(CDCl$_3$): 8.50, 7.95, 6.94, (m, 7H, ArH, pyrH), 2.33 (s, 6H, N=CCH$_3$), 2.28 (s, 6H, CCH$_3$), 2.05 (s, 12H, CCH$_3$).

Mass spectrum: m/z 397[M]+.

9.2—Preparation of 2,6-diacetylpyridinebis(2,4,6-trimethylanil)FeCl$_2$

The procedure was as for Example 4.2 except that 2,6-diacetylpyridinebis(2,4,6-trimethylanil) was employed instead of 2,6-diacetylpyridinebis(2-tert.-butylanil). The yield was 64% of theoretical.

Mass spectrum: m/z 523 [M]+, 488 [M–Cl]+, 453 [M–Cl$_2$]+.

Examples 14 to 25

These Examples are a series of tests wherein ethylene or ethylene/1-hexene is polymerised under 10 bars ethylene pressure using the catalysts of the present invention under "slurry" polymerisation conditions.

Catalyst Preparation

The transition metal complexes employed as catalyst in Examples 14 to 25 were as follows:

In Examples 14 and 15 the complex was 2,6-diacetylpyridinebis(2,6-diisopropylanil)FeCl$_2$ prepared as described in Example 1 (Formula D compound).

In Examples 16 to 20 the complex was was 2,6-diacetylpyridinebis(2,6-dimethylanil)FeCl$_2$ prepared as described in Example 8.

In Example 21 the complex was 2,6-diacetylpyridinebis(2,4-dimethylanil)FeCl$_2$ prepared as described in Example 7.

In Examples 22 to 24 the complex was 2,6-diacetylpyridinebis(2,4,6-trimethylanil)FeCl$_2$ prepared as described in Example 9.

In Example 25 the complex was 2,6-diacetylpyridinebis(2,6-diisopropylanil)CoCl$_2$ prepared as described in Example 3 (Formula K).

Catalyst Activation

The transition metal complex was dissolved in toluene (previously dried over sodium metal) under a nitrogen atmosphere and there was added a solution of activator (cocatalyst) at ambient temperature. The mixture was stirred at room temperature then an aliquot transferred to the injection unit of a polymerisation reactor. The quantities of reagents employed in the catalyst activation are set out in the following Table. All operations were conducted under a nitrogen atmosphere unless specified. "MAO" is methyl aluminoxane (1.78M in toluene supplied by Witco). "MMAO" is modified methyl aluminoxane (10% w/w in heptane—supplied by Witco) were used as purchased. Triisobutylaluminium (Al(iBu)$_3$ as a 1M solution in toluene was supplied by Aldrich.

Polymerisation of Ethylene

A 1 liter reactor was baked out under a nitrogen flow for at least 1 hour at >85° C. The reactor was then cooled to 50° C. Isobutane (0.5 liter) and triisobutylaluminium were then added and the reactor was boxed in nitrogen. The alkyl aluminium was allowed to scavenge for poisons in the reactor for at least 1 hour. Ethylene was introduced into the reactor until a predetermined over-pressure was achieved then the catalyst solution was injected under nitrogen. The reactor pressure was maintained constant throughout the polymerisation run by computer controlled addition of additional ethylene. The polymerisation time was 1 hour. Upon termination of the run the reactor contents were isolated, washed with acidified methanol (50 ml HCl/2.5 l methanol) and water/ethanol (4:1 v/v) and dried under vacuum, at 40° C., for 16 hours.

Copolymerisation of Ethylene/1-Hexene (Example 19)

A 1 liter reactor was baked out under a nitrogen flow for at least 1 hour at >85° C. The reactor was then cooled to 50° C., isobutane (0.5 liter), 1-hexene and triisobutylaluminium were then added and the reactor was boxed in nitrogen. The alkyl aluminium was allowed to scavenge for poisons in the reactor for at least 1 hour. Ethylene was introduced into the reactor until a predetermined over-pressure was achieved then the catalyst solution was injected under nitrogen. The reactor pressure was maintained constant throughout the polymerisation run by computer controlled addition of ethylene. The polymerisation time was 1 hour. Upon termination of the run the reactor contents were isolated, washed with acidified methanol (50 ml HCl/2.5 l methanol) and water/ethanol (4:1 v/v) and dried under vacuum, at 40° C., for 16 hours.

Data from the polymerisation tests are set out below in the Table.

TABLE

| Ex. No. | Metal Complex (mg) | [Metal] ($\mu$mols) | Co-Catalyst | Co-Catalyst (ml) | [Al] (mmols) | [Fe]:[Al] | Toluene (ml) | Solution Molarity (M) |
|---|---|---|---|---|---|---|---|---|
| 14 | 3 | 5 | MAO | 2.78 | 5 | 1:1000 | 20 | 0.0025 |
| 15 | 3 | 5 | MAO | 2.78 | 5 | 1:1000 | 20 | 0.0025 |
| 16 | 1.5 | 3 | MAO | 1.70 | 3 | 1:1000 | 10 | 0.0025 |
| 17 | 1.5 | 3 | MMAO | 3.93 | 3 | 1:1000 | 10 | 0.0025 |
| 18 | 1.5 | 3 | MAO | 1.70 | 3 | 1:1000 | 50 | 0.0006 |
| 19 | 1.5 | 3 | MAO | 1.70 | 3 | 1:1000 | 10 | 0.0025 |
| 20 | 1.5 | 3 | MAO | 0.17 | 3 | 1:1000 | 10 | 0.0025 |
| 21 | 1.5 | 3 | MAO | 1.70 | 3 | 1:1000 | 10 | 0.0025 |
| 22 | 3 | 6 | MAO | 3.22 | 6 | 1:1000 | 20 | 0.003 |
| 23 | 1.5 | 3 | MAO | 1.61 | 3 | 1:1000 | 10 | 0.003 |
| 24 | 3 | 6 | MAO | 0.32 | 0.3 | 1:100 | 20 | 0.003 |
| 25 | 3 | 5 | MAO | 2.78 | 5 | 1:1000 | 20 | 0.0025 |

Polymerisation Tests

The reagents used in the polymerisation tests were Ethylene Grade 3.5 (supplied by Air Products), hexene (supplied by Aldrich) distilled over sodium/nitrogen and triisobutylaluminium (1M in hexanes, supplied by Aldrich).

TABLE

| Ex. No. | [metal] (µmols) | metal/ aluminoxane Ratio | C$_2$H$_4$ Bar | hexene (ml) | Al(iBu)$_3$ (ml) | polymerisation Temp. (° K.) | polymer (g) | activity (g/mmol M/h/b) |
|---|---|---|---|---|---|---|---|---|
| 14 | 0.3  | 1:1000 | 10 | 0  | 3 | 323 | 26.9  | 5430  |
| 15 | 0.3  | 1:1000 | 10 | 0  | 3 | 298 | 45.0  | 9090  |
| 16 | 0.3  | 1:1000 | 10 | 0  | 3 | 323 | 56.5  | 9340  |
| 17 | 0.3  | 1:1000 | 10 | 0  | 3 | 323 | 57.4  | 9510  |
| 18 | 0.13 | 1:1000 | 10 | 0  | 3 | 323 | 3.3   | 2540  |
| 19 | 0.3  | 1:1000 | 10 | 50 | 3 | 323 | 67.6  | 16690 |
| 20 | 0.3  | 1:1000 | 10 | 0  | 3 | 323 | 74.5  | 12310 |
| 21 | 0.3  | 1:1000 | 10 | 0  | 3 | 323 | 7.8   | 1280  |
| 22 | 0.3  | 1:1000 | 10 | 0  | 3 | 323 | 63.1  | 11020 |
| 23 | 0.06 | 1:1000 | 10 | 0  | 3 | 323 | 55.7  | 48690 |
| 24 | 0.3  | 1:100  | 2  | 0  | 2 | 323 | 18.21 | 15150 |
| 25 | 0.3  | 1:1000 | 10 | 0  | 3 | 323 | 3.7   | 450   |

Molecular weight data of the polymers obtained from Examples 14 to 25 are set out in the Table below.

TABLE

| Ex. No. | Mw | Mn | Mpeak | PD |
|---|---|---|---|---|
| 14 | 611000 | 64000  | 246000 | 9.5  |
| 15 | 857000 | 212000 | 451000 | 4.0  |
| 16 | 242000 | 9600   | 16000  | 25.3 |
| 17 | 278000 | 5700   | 1300   | 48.7 |
| 18 | 366000 | 50000  | 102000 | 7.3  |
| 19 | 377000 | 6500   | 43000  | 57.7 |
| 21 | 470    | 360    | 370    | 1.3  |
| 25 | 14000  | 4200   | 12000  | 3.3  |

Examples 26 and 27
Gas Phase Polymerisation Tests with Supported Catalysts

Examples 26 and 27 illustrate the use of the catalysts of the present invention supported on silica support material. Example 26 employs 2,6-diacetylpyridinebis(2,6-diisopropylanil)FeCl$_2$, and Example 27 employs 2,6-diacetylpyridinebis(2,4,6-trimethylanil)FeCl$_2$ as the transition metal complex compound.

Example 26
Preparation of the Supported Catalyst 2,6-Diacetylpyridinebis(2,6-diisopropylanil)FeCl$_2$ was prepared as described in Example 1. Silica (1.03 g ES70, supplied by Crosfield), which had been heated under flowing nitrogen at 700° C., was placed in a Schlenk tube, and toluene (10 ml) was added. The mixture was heated to 50° C. To a solution of 2,6-diacetylpyridinebis(2,6-diisopropylanil)FeCl$_2$ (0.036 g) in toluene (10 ml) was added methylaluminoxane (5 ml, 1.78M in toluene, supplied by Witco). This mixture was heated at 50° C. and then transferred to the silica/toluene mixture. The silica/MAO/toluene mixture was maintained at 50° C., with regular stirring, for 1 hour before the toluene was removed, at 65° C., under vacuum to yield a free flowing powder.

Example 27
Preparation of the Supported Catalyst 2,6-Diacetylpyridinebis(2,4,6-trimethylanil)FeCl$_2$ was prepared as described in Example 9. Silica (1.38 g ES70, supplied by Crosfield), which had been heated under flowing nitrogen at 700° C., was placed in a Schlenk tube and toluene (10 ml) was added. To a solution of 2,6-diacetylpyridinebis(2,4,6-trimethylanil)FeCl$_2$ (0.041 g) in toluene (10 ml) was added methylaluminoxane (13.2 ml, 1.78M in toluene, supplied by Witco). This mixture was heated at 40° C. for 30 minutes to dissolve as much of the iron complex as possible. The solution was then transferred to the silica/toluene. The silica/MAO/toluene mixre was maintained at 40° C., with regular stirring, for 30 minutes before the toluene was removed, at 40° C., under vacuum to yield a free flowing powder. Analysis of the solid gave 16.9% w/w Al and 0.144% w/w Fe.

Polymerisation Tests—Examples 26 and 27

The reagents used in the polymerisation tests were: hydrogen Grade 6.0 (supplied by Air Products): ethylene Grade 3.5 (supplied by Air Products): hexene (supplied by Aldrich) distilled over sodium/nitrogen: dried pentane (supplied by Aldrich): methylaluminium (2M in hexanes, supplied by Aldrich): and triisobutylaluminium (1M in hexanes, supplied by Aldrich).

A 3 liter reactor was baked out under flowing nitrogen for at least 1 hour at 77–85° C. before powdered sodium chloride (300 g, predried under vacuum, 160° C., >4 hours) was added. The sodium chloride was used as a fluidisable/stirrable start-up charge powder for the gas phase polymerisation. Trimethyl aluminium (3 ml, 2M in hexanes) was added to the reactor and was boxed in nitrogen. The alkyl aluminium was allowed to scavenge for poisons in the reactor for between ½–1 hour before being vented using 4×4 bar nitrogen purges. The gas phase composition to be used for the polymerisation was introduced into the reactor and preheated to 77° C. prior to injection of the catalyst composition. The catalyst (0.18–0.22 g) was injected under nitrogen and the temperature then adjusted to 80° C. The ratio of hexene and/or hydrogen to ethylene during the polymerisation was kept constant by monitoring the gas phase composition by mass spectrometer and adjusting the balance as required. The polymerisation tests were allowed to continue for between 1 to 2 hours before being terminated by purging the reactants from the reactor with nitrogen and reducing the temperature to <30° C. The produced polymer was washed with water to remove the sodium chloride, then with acidified methanol (50 ml HCl/2.5 L methanol) and finally with water/ethanol (4:1 v/v). The polymer was dried under vacuum, at 40° C., for 16 hours. Several Runs, using a variety of operating conditions were carried out with each of the catalysts of Examples 26 and 27. All the polymerisation tests were carried out at a polymerisation temperature of 80° C. and at an ethylene pressure of 8 bars. The polymerisation conditions are set out in the following Table.

TABLE

| Ex/Run | Metal (% w/w) | MAO/Metal Ratio | other co-catalyst/ (mmols) | $H_2$ (bar) | hexene (bar) | pentane (bar) | Run time (min) | Activity g/mmol M/h/b |
|---|---|---|---|---|---|---|---|---|
| 26.1 | 0.21 | 150 | **** | **** | **** | **** | 75 | 77 |
| 26.2 | 0.21 | 150 | **** | **** | 0.195 | **** | 90 | 77 |
| 26.3 | 0.21 | 150 | TMA/6 | **** | **** | **** | 60 | 149 |
| 26.4 | 0.21 | 150 | TMA/6 | 0.75 | **** | **** | 60 | 318 |
| 27.1 | 0.144 | 300 | **** | **** | **** | **** | 60 | 611 |
| 27.2 | 0.144 | 300 | TMA/6 | 0.5 | **** | **** | 60 | 832 |
| 27.3 | 0.144 | 300 | TMA/6 | 0.5 | 0.2 | **** | 60 | 1054 |
| 27.4 | 0.144 | 300 | TMA/6 | 0.5 | **** | 2.4 | 60 | 1800 |
| 27.5 | 0.144 | 300 | TiBA/3 | **** | **** | **** | 60 | 713 |
| 27.6 | 0.144 | 300 | **** | 3 | **** | **** | 60 | 501 |
| 27.7 | 0.144 | 300 | **** | **** | 0.86 | **** | 60 | 418 |

Molecular weight data on the polymer products is set out in the Table below.

| Run | Catalyst | Mw | Mn | Mpeak | Polydispersity |
|---|---|---|---|---|---|
| 26.1 | Ex 26 | | | | |
| 26.2 | Ex 26 | 892000 | 106000 | 332000 | 8.4 |
| 26.3 | Ex 26 | 278000 | 8400 | 95000 | 33.0 |
| 26.4 | Ex 26 | 195000 | 7200 | 43000 | 27.0 |
| 27.1 | Ex 27 | 324000 | 9300 | 134000 | 34.6 |
| 27.2 | Ex 27 | 223000 | 18000 | 42000 | 12.3 |
| 27.3 | Ex 27 | 77000 | 6000 | 21000 | 12.8 |
| 27.4 | Ex 27 | 154000 | 5700 | 28000 | 26.9 |
| 27.5 | Ex 27 | 207000 | 4800 | 86000 | 43.1 |
| 27.6 | Ex 27 | 69000 | 5400 | 14000 | 12.7 |
| 27.7 | Ex 27 | 127000 | 14000 | 51000 | 9.3 |

Example 32

32.1—Preparation of a Supported Ziegler Catalyst Component

Silica (20 kg), grade ES 70 supplied by Crosfield, which had been dried at 800° C. for 5 hours in flowing nitrogen, was slurried in hexane (110 liters) and hexamethyidisilazane (30 moles), supplied by Fluka, was added with stirring at 50° C. Dry hexane (120 liters) was added with stirring, the solid allowed to settle, the supernatant liquid removed by decantation and further dry hexane (130 liters) was added with stirring. The hexane washing was repeated a further 3 times. Dibutylmagnesium (30 moles), supplied by FMC, was added and stirred for 1 hour at 50° C. Tertiary butyl chloride (60 moles) was added and stirred for 1 hour at 50° C. To this slurry was added an equimolar mixture of titanium tetra-chloride (3 moles), and titanium tetra-n-propoxide (3 moles) with stirring at 50° C. for 2 hours, followed by 5 washings with dry hexane (130 liters). The slurry was dried under a flowing nitrogen stream to give a solid, silica supported Ziegler catalyst component.

32.2—Preparation of a Mixed Catalyst Containing a Ziegler Component and a Transition Metal Compound of the Present Invention A solution of methylaluminoxane ("MAO", 10.2 mmol) as a 10% wt solution in toluene, supplied by Witco, was added to a suspension of 2,6-diacetylpyridinebis(2,4,6-trimethylanil)FeCl$_2$ (0.07 mmol in 5 ml dry toluene), prepared as in Example 9, and the mixture shaken for 5 minutes. This solution was then added to 2.0 g of the silica supported Ziegler catalyst prepared above (Example 32.1), the mixture shaken for 2 hours at 20° C. and then the solvent removed under reduced pressure at 20° C. to yield the mixed catalyst as a free flowing powder.

32.3—Polymerisation of Ethylene/hexene Mixture Using the Mixed Catalyst

A 3 liter reactor equipped with a helical stirrer was heated to 95° C. for 1 hour with dry nitrogen flowing through. The temperature was reduced to 50° C. and dry sodium chloride (300 g) was then added with trimethylaluminium (TMA) solution (2 ml of 2 molar TMA in hexane) and the reactor heated at 85° C. for 2 hours. The reactor was purged with nitrogen, cooled to 50° C. and TMA solution (3 ml of 2 molar TMA in hexane) added. The temperature was raised to 77° C. and hydrogen (0.5 bar) and ethylene (8 bar) added prior to the addition of 1-hexene (2.6 ml). Reaction was started by injection into the reactor of the mixed catalyst (0.20 g) prepared above. The temperature was maintained at 80° C. and ethylene added to maintain constant pressure. The gas phase was monitored by a mass spectrometer and hydrogen and 1-hexene added as necessary to maintain constant gas phase concentrations of these components. The polymerisation was earied out for 90 minutes. The polymer was washed with water to remove the sodium chloride, then with acidified methanol (50 ml HCl/2.5 liters methanol) and finally with water/ethanol (4:1 v/v ). The polymer was dried under vacuum, at 40° C. for 16 hours. 111 g of dried polymer was produced. The polymer had a broad molecular weight distribution (as determined by gel permeation chromatography. The polydispersity (Mw/Mn) was 28.5.

Example 33

33.1—Pre-impregnation of Support with Activator Compound

All the following operations were conducted under a nitrogen atmosphere unless stated. Silica (Crosfield grade ES70X) was heated under flowing nitrogen at 250° for 16 hours. A sample of this silica (2.5 g) was placed in a Schlenk tube and had 12.1 ml of 1.78M methylaluminoxane, MAO (supplied by Witco) added to it to form a slurry. The slurry was heated for 4 hours at 50° C. before being left for 10 days at room temperature. The supernatant liquid above the silica was removed and the silica/MAO washed three times with toluene (3×10 ml) at room temperature, removing the supernatant solution each time.

33.2—Supporting the Catalyst (2,6-diacetylpyridinebis(2,4,6 trimethyl anil) iron dichloride (0.101 g) (prepared as described in Example 9) was slurried in toluene (20 ml), at room temperature, and added to the silica/MAO. The mixture was occasionally shaken over a 1 hour period. The supernatant solution was removed and the silica/MAO/Fe complex was washed with toluene until the filtrate was colourless. The solid was dried under vacuum at 50° C.

33.3—Gas Phase Polymerisation of Ethylene

A 3 liter reactor was baked out under flowing nitrogen for at least 1 hour at 77° C. before sodium chloride (300 g, <1 mm diameter particles, predried under vacuum, 160° C., >4 hours) was added. The sodium chloride was employed merely as a standard "charge powder" for the gas phase polymerisation reactor. Trimethyl aluminium (3 ml, 2M in hexanes, supplied by Aldrich) was added to the reactor which was then closed. The alkyl aluminium was allowed to scavenge for poisons in the reactor for ½ hour before being vented by successive pressurising and purging the reactor with 4 bar of nitrogen. Ethylene (Grade 3.5, supplied by Air Products) was added to the reactor to give a pressure of 8 bar, at 77° C., prior to catalyst injection. The supported catalyst (0.215 g) prepared as described in Example 33.2 was injected into the reactor under nitrogen and the temperature then adjusted to 80° C. The polymerisation was allowed to continue for 5 hours before being terminated by purging the ethylene from the reactor, using nitrogen, and reducing the temperature to below 30° C. The polymer was washed with water to remove the sodium chloride, then with acidified methanol (50 ml HCl/2.5 liters methanol) and finally with water/ethanol (4:1 v/v). The polymer was dried under vacuum, at 40° C., for 16 hours. 161 g of dried polymer was produced.

Examples 35 to 38

These illustrate the preparation of supported catalysts in accordance with the present invention and their use in the polymerisation of ethylene under "slurry" polymerisation conditions.

Example 35

35.1—Preparation of 2,6-diacetylpyridinebis(2,4,6 trimethal anil) Iron Dichloride Supported on MAO/silica Silica support material (grade ES70X supplied by Crosfield) was heated under flowing nitrogen at 250° C. for 16 hours. A sample of this silica was placed in a Scheak tube and 12.1 ml of 1.78M methylaluminoxane ("MAO" supplied by Witco) was added to it to form a slurry. The slurry was heated for 4 hours at 50° C. before being left for 10 days at room temperature. The supernatant liquid above the silica was then removed and the silica/MAO washed 3 times with toluene (10 ml) at room temperature, removing the supernatant solution each time. 2,6-diacetylpyridinebis(2,4,6 trimethyl anil) iron dichloride complex (0.101 g) was slurried in toluene (20 ml), at room temperature, and added to the silica./MAO. The mixture was occasionally shaken over a 1 hour period. The supernatant solution was removed and the produced silica-supported MAO/Fe complex washed with toluene until the initial washings, which were light orange in colour, became clear and free from colour. The produced silica-supported catalyst solid was dried under vacuum at 50° C.

35.3—Polymerisation of Ethylene

A 1 liter reactor was heated under flowing nitrogen for 3 hours at 80° C. The reactor was cooled to less than 30° C. and 500 ml of isobutane added. Trimethyl aluminium (3 ml of 2M in hexanes) was added to the reactor and this was then heated to 80° C. The pressure in the reactor increased to 13.8 bar and then ethylene was admitted to give a total pressure of 23.8 bar. The supported catalyst prepared in 35.1 above (0.201 g of the supported catalyst solid in toluene slurry) was injected into the reactor under nitrogen causing the reactor pressure to increase to 25.4 bar. The catalyst activity was slightly too high for the ethylene inlet flow to keep the pressure constant and this was therefore allowed to fall to 23.2 bar. The ethylene pressure present in the reactor for the majority of the polymerisation was estimated to be 7.8 bar. The test was terminated after 1.75 hours and the polymer washed with methanol/HCl (2.5 liters/50 ml), then water/ethanol (4:1 v/v) and dried under vacuum at 40° C. 166 g of dry polymer was recovered. Analysis of the polymer by GPC indicated Mw and Mn to be 182000 and 11000 respectively.

Example 36

36.1—Preparation of 2,6-diacetylpyridinebis(2,4,6 trimethyl anil) Iron Dichloride Supported on MAO/silica A portion (about 1–1.5 g) of the supported catalyst prepared in Example 35.1 was washed with 5×10 ml aliquots of toluene at 100° C. The initial washings had a deep orange colour and this colouration became less with each subsequent washing until the final washing was clear of colour. The solid was dried under vacuum at 100° C. to provide free-flowing solid supported catalyst.

36.2—Polymerisation of Ethylene

A 1 liter reactor was heated under flowing nitrogen for 1 hour at 75° C. Trimethyl aluminium (3 ml of 2M in hexanes) was added to the reactor which was then cooled to 50° C. Isobutane (500 ml) was added to the reactor and the temperature increased to 76° C. The pressure in the reactor increased to 13 bar. Ethylene was admitted to the reactor to give 21 bar total pressure (8 bar ethylene). The supported catalyst prepared in 26.1 above (0.11 g in toluene slurry) was injected into the reactor and the pressure increase taken into account during control of the reactor pressure during the test. The temperature was increased to 80° C. After 1 hour a further aliquot of the same catalyst was injected (0.22 g in hexane slurry) and the test continued for a further 3.5 hours.

25 g of polymer was recovered. Analysis of the polymer by GPC indicated Mw and Mn to be 343000 and 35000 respectively.

Example 37

37.1—Preparation of 2,6-diacetylpyridinebis(2,4,6 trimethyl anil) Iron Dichloride Supported on MAO/silica Methyl aluminoxane (24 ml of 1.78M in toluene, supplied by Witco) was added to silica (5 g of grade ES70X supplied by Crosfield) which had been heated under flowing nitrogen at 250° C. The silica/MAO was heated at 80° C. for 1 hour before being washed toluene (5×10 ml aliquots). Half of the produced silica/MAO slurry, cooled to room temperature, was used for the next stage of the catalyst preparation (the other half was put aside for use in Example 38). 2,6-diacetylpyridinebis(2,4,6 trimethyl anil) iron dichloride (73 mg) was slurried in toluene and transferred to the half-portion of silica/MAO/toluene and left to react for 2 hours with occasional mixing. The silica/MAO/Fe complex was washed with toluene (3×10 ml aliquots) at room temperature and then with hexane (2×10 ml aliquots) at room temperature to remove the toluene before finally being washed with hexane at 80° C. (3×10 ml aliquots). The produced supported catalyst solid was dried under vacuum at room temperature.

37.2—Polymerisation of Ethylene

A 1 liter reactor was heated under flowing nitrogen for 1 hour at 80° C. The reactor was cooled to less than 30° C. and 500 ml of isobutane added. The reactor was heated to 77° C. and the pressure increased to 13.8 bar. Ethylene was added to give 21.8 bar total pressure (8 bar ethylene). Triisobutyl aluminium (5 ml of 1M in hexanes) was added to the reactor and after 20 minutes the supported catalyst prepared in 37.1 above (0.14 g in hexane slurry) was injected into the reactor and the pressure increase taken into account during control of the reactor pressure during the test. The temperature was increased to 80° C. After 5 hours the polymerisation was terminated. 138 g of polymer was recovered. Analysis of the polymer by GPC indicated Mw and Mn to be 567000 and 53000 respectively.

37.3—Polymerisation of Ethylene

A 1 liter reactor was heated under flowing nitrogen for 1 hour at 78° C. The reactor was cooled to less than 30° C. and 500 ml of isobutane added. Triisobutyl aluminium (3 ml of 1M in hexanes) was added to the reactor which was then heated to 78° C. and the pressure increased to 12.1 bar. Ethylene was added to give 32.0 bar total pressure (19.9 bar ethylene). The supported catalyst prepared in 37.1 above (0.0925 g, slurried in hexane) was injected into the reactor and the total pressure was controlled at 31.2 bar. The ethylene pressure during the polymerisation was estimated to be approximately 19.1 bar. Polymerisation was allowed to continue for 80 minutes. 181 g of polymer was recovered. Analysis of the polymer by GPC indicated Mw and Mn to be 595000 and 44000 respectively.

37.4—Polymerisation of Ethylene

A 1 liter reactor was heated under flowing nitrogen for 1 hour at 80° C. before being cooled to less than 30° C. Triisobutyl aluminium (3 ml of 1M in hexanes) was added to the reactor followed by 500 ml of isobutane. The reactor was heated to 78° C. and the pressure increased to 13.5 bar. Ethylene was added to give 17.6 bar total pressure (4.1 bar ethylene). The supported catalyst prepared in 37.1 above (0.15 g, slurried in hexane) was injected into the reactor. The ethylene pressure during the polymerisation was estimated to be approximately 4.7 bar. Polymerisation was allowed to continue for 80 minutes. 21 g of polymer was recovered. Analysis of the polymer by GPC indicated Mw and Mn to be 347000 and 26000 respectively.

Example 38

38.1—Preparation of 2,6-diacetylpyridinebis(2,6 diisopropyl anil) Cobalt Dichloride Supported on MAO/silica The second half of the silica/MAO made in Example 37.1 was dried under vacuum. An aliquot of the dried silica/MAO (1 g) was placed in to a Schlenk tube and 2,6-diacetylpyridinebis(2,6 diisopropyl anil) cobalt dichloride (40 mg) added to this as a dry powder. Hexane (10 ml) was then added to the Schlenk tube and the cobalt complex and silica/MAO slurried together for 1 hour at room temperature. The mixture was dried under vacuum at room temperature to leave the produced supported catalyst as a dry, free flowing powder.

38.2—Polymerisation of Ethylene

A 1 liter reactor was heated under flowing nitrogen for 1 hour at 80° C. before being cooled to 30° C. Hexene (250 ml), triisobutyl aluminium (3 ml of 1M in hexanes) and 250 ml of isobutane were added to the reactor. The reactor was heated to 80° C. and the pressure increased to 7.1 bar. Ethylene was added to give 19.2 bar total pressure (12.1 bar ethylene). The supported catalyst prepared in above (0.245 g, slurried in hexane) was injected into the reactor and the pressure increase taken into account during control of the reactor pressure during the test. Polymerisation was allowed to continue for 330 minutes. 3.3 g of polymer was recovered. Analysis of the polymer by GPC indicated Mw=5300 and
Mn=1500.

Example 39

Polymerisation of Ethylene in Slurry Phase Using a Supported Catalyst

A series of polymerisation tests was carried out using a catalyst based on a supported 2,6-diacetylpyridinebis(2,4,6 trimethyl anil) iron dichloride.

Example 39.1

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.2 bar. Ethylene was added to give 26.2 bar total pressure. The catalyst of Example 37.1 (0.097 g, slurried in hexane) was injected into the reactor. The reactor pressure was controlled at 26.0 bar during the test (ethylene pressure estimated to be approximately 12.8 bar) and the temperature adjusted to 80° C. Polymerisation was allowed to continue for 60 minutes. 78 g of polymer was recovered. Analysis of the polymer by GPC indicated Mw and Mn to be 528000 and 40000 respectively.

Example 39.2

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.4 bar. Ethylene was added to give 21.2 bar total pressure. The catalyst of Example 37.1 (0.124 g, slurried in hexane) was injected into the reactor. The ethylene pressure was estimated to be approximately 8.1 bar during the polymerisation and the temperature adjusted to 80° C. Polymerisation was allowed to continue for 60 minutes. 47 g of polymer was recovered. Analysis of the polymer by GPC indicated Mw and Mn to be 376000 and 40000 respectively.

Example 39.3

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 13.0 bar. Ethylene was added to give 26.0 bar total pressure. The catalyst of Example 37.1 (0.0966 g, slurried in hexane and 0.25 ml of NN dimethylaniline for 20 minutes) was injected into the reactor. The pressure in the reactor was allowed to fall to 22.5 bar to reduce the activity of the catalyst. The ethylene pressure in the reactor during the majority of the polymerisation was estimated to be 9.0 bar. Polymerisation was allowed to continue for 60 minutes. 88 g of polymer was recovered. Analysis of the polymer by GPC indicated Mw and Mn to be 430000 and 35000 respectively.

Example 39.4

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 12.7 bar. Ethylene was added to give 14.7 bar total pressure. The catalyst of Example 37.1 (0.104 g, slurried in hexane) was injected into the reactor. The ethylene pressure during the polymerisation was estimated to be approximately 2.2 bar. Polymerisation was allowed to continue for 60 minutes. 4.8 g of polymer was recovered. Analysis of the polymer by GPC indicated Mw and Mn to be 340000 and 36000 respectively.

Example 40

Polymerisation of Ethylene in Slurry Phase Using a Supported Catalyst

A series of polymerisation tests was carried out using a catalyst based on a supported 2,6-diacetylpyridinebis(2,4,6 trimethyl anil) iron dichloride.

Example 40.1

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.2 bar. Ethylene was added to give 26.2 bar total pressure. The catalyst of Example 37.1 (0.097 g, slurried in hexane) was injected into the reactor. The reactor pressure was controlled at 26.0 bar during the test (ethylene pressure estimated to be approximately 12.8 bar) and the temperature adjusted to 80° C. Polymerisation was allowed to continue for 60 minutes. 78 g of polymer was recovered. Analysis of the polymer by GPC indicated Mw and Mn to be 528000 and 40000 respectively.

Example 40.2

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.4 bar. Ethylene was added to give 21.2 bar total pressure. The catalyst of Example 37.1 (0.124 g, slurried in hexane) was injected into the reactor. The ethylene pressure was estimated to be approximately 8.1 bar during the polymerisation and the temperature adjusted to 80° C. Polymerisation was allowed to continue for 60 minutes. 47 g of polymer was recovered. Analysis of the polymer by GPC indicated Mw and Mn to be 376000 and 40000 respectively.

Example 40.3

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 13.0 bar. Ethylene was added to give 26.0 bar total pressure. The catalyst of Example 37.1 (0.0966 g, slurried in hexane and 0.25 ml of NN dimethylaniline for 20 minutes) was injected into the reactor. The pressure in the reactor was allowed to fall to 22.5 bar to reduce the activity of the catalyst. The ethylene pressure in the reactor during the majority of the polymerisation was estimated to be 9.0 bar. Polymerisation was allowed to continue for 60 minutes. 88 g of polymer was recovered. Analysis of the polymer by GPC indicated Mw and Mn to be 430000 and 35000 respectively.

Example 40.4

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 12.7 bar. Ethylene was added to give 14.7 bar total pressure. The catalyst of Example 37.1 (0.104 g, slurried in hexane) was injected into the reactor. The ethylene pressure during the polymerisation was estimated to be approximately 2.2 bar. Polymerisation was allowed to continue for 60 minutes. 4.8 g of polymer was recovered. Analysis of the polymer by GPC indicated Mw and Mn to be 340000 and 36000 respectively.

Example 41

This Example shows the use of a combination of a metallocene-type catalyst with a catalyst based on an iron complex of the present invention for polymerising ethylene under slurry conditions.

41.1—Preparation of a Supported Metallocene Catalyst

To silica (Crosfield grade ES70, previously calcined at 200° C. in flowing $N_2$ for 5 hrs) was added a toluene solution of methylaluminoxane (MAO) containing dissolved bis(n-butylcyclopentadienyl)$ZrCl_2$. The amounts used were 2.5 mmuol MAO per gram of silica and 0.05 mmol metallocene per gram silica. The resulting slurry was stirred gently for at least 1 hour before being dried under reduced pressure to give a free flowing powder.

41.2—Preparation of the Combined Metallocene/Fe-complex Catalyst

The supported metallocene catalyst (2.5 g) prepared as described in step 41.1 above was placed in a Schlenk tubeand a slurry of 2,6-diacetylpyridinebis(2,4,6 trimethyl anil) iron dichloride (73 mg) in hexane (10 ml) was added thereto at ambient temperature. The mixture was heated to 80° C. and left for 90 minutes with occasional shaking to maintain a well-mixed solution. There was no coloration evident in the supernatant solution above the solid. The produced catalyst was dried at 80° C. under vacuum to leave a dry free flowing powder.

41.3—Polymerisation of Ethylene

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 77° C. and the pressure increased to 12.9 bar. Ethylene was added to give 20.9 bar total pressure. The catalyst (0.100 g, slurried in hexane) prepared as described in 41.2 above was injected into the reactor. The ethylene pressure during the polymerisation was estimated to be approximately 8 bar. Polymerisation was allowed to continue for 60 minutes. 96 g of polymer was recovered. Analysis of the polymer by GPC indicated Mw and Mn to be 471000 and 30000 respectively.

41.4—Comparative

This shows the polymerisation of ethylene using only the supported metallocene catalyst described in step 41.1.

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 75° C. and the pressure increased to 12.7 bar. Ethylene was added to give 20.7 bar total pressure. The supported metallocene catalyst (0.094 g, slurried in hexane) prepared in step 41.1 above was injected into the reactor. The ethylene pressure during the polymerisation was estimated to be approximately 8 bar. Polymerisation was allowed to continue for 60 minutes. 49 g of polymer was recovered. Analysis of the polymer by GPC indicated Mw and Mn to be 142000 and 53000 respectively.

Example 42

Gas Phase Polymerisation

This Example shows the use of a combination of a metallocene-type catalyst with a catalyst based on an iron complex of the present invention for polymerising ethylene under gas phase polymerisation conditions.

A 3 liter reactor was baked out under flowing nitrogen for least 1 hour at 78° C. before being cooled to 30° C. Powdery sodium chloride (300 g) charge powder having an average particle diameter of less than 1 millimeter 1 mm and having been predried under vacuum at 160° C. for more than 4 hours, was added followed by trimethyl aluminium (3 ml, 2M in hexanes, supplied by Aldrich). The reactor was then closed and heated to 78° C. The alkyl aluminium was allowed to scavenge any poisons present in the reactor for 90 minutes. The reactor was then purged, four times, by pressurising to 4 bars with nitrogen, and then venting. Hydrogen was added to the reactor give 0.08 bar pressure followed by ethylene (8 bar). The catalyst (0.20 g,) as prepared in step 41.3 above was injected under nitrogen and the temperature then adjusted to 80° C. The polymerisation was allowed to continue for 60 minutes before being terminated by purging the ethylene from the reactor, using nitrogen, and reducing the temperature to below 30° C. The polymer was washed with water to remove the sodium chloride, then with acidified methanol (50 ml HCl/2.5 liters methanol) and finally with water/ethanol (4:1 v/v). The polymer was dried under vacuum, at 40° C., for 16 hours. 64 g of dried polymer was produced. The GPC (gel permeation chromatogram) was run for the polymer product. The produced GPC curve was distinctly bimodal with Mw=253000 and a polydispersity of 64.9.

Example 43

Slurry Polymerisation Using 2,6-diacetylpyridinebis (2,4,6-trimethylanil)$FeCl_2$ with and without TIBA This Example shows the positive effect on activity of the catalyst obtained by incorporating triisobutyl aluminium (TIBA) as a cocatalyst in comparison with the complete absence of a separately added alkylaluminium compound as defined as component (3) in the present invention. The catalyst employed was that prepared in Example 37.1 above.

43.1—Polymerisation with TIBA

A 2.3 liter reactor equipped with a stirrer and jacketed for temperature control was heated under dry nitrogen at 110° C. for 1 hour. It was then cooled to 85° C., and a triisobutyl aluminium solution in dry hexane injected under nitrogen. The reactor was then charged with 1 liter of dry isobutane. The stirred reactor contents were pressurised to 600 psig by addition of dry ethylene, with the temperature maintained at 85° C. The catalyst of Example 37.1 was injected into the reactor under nitrogen, and the injection line purged with approximately 50 ml of isobutane. Reaction was then controlled at 600 psig by continuous ethylene addition, and conversion monitored from ethylene consumption. The polymerisation was conducted for the time specified in the Table below, at which point ethylene addition was stopped and the reactor vented to atmospheric pressure, prior to polymer recovery and stabilisation. The polymer was stabilised by addition of a dilute acetone solution of Irganox 1076 to give 0.15% additive in polymer. Reaction conditions, yield and activity are given in the Table below.

43.2—Polymerisation without TIBA (Comparative)

The procedure of Example 43.1 was repeated except that no TIBA was added. Details are also shown in the Table below, from where it can be seen that addition of TIBA to the catalyst results in a substantial improvement in activity.

| Ex | Catalyst Weight g | TIBA (1 M) ml | Temp ° C. | Time mins | Yield g | Prodty g/g | Activity g/g/hr |
|---|---|---|---|---|---|---|---|
| 43.1 | 0.1 | 3 | 80 | 35 | 530 | 5300 | 9085 |
| 43.2 | 0.103 | 0 | 80 | 55 | 495 | 4805 | 5242 |

A comparison of polymerisation with and without TIBA was also carried out at pilot plant scale.

43.3—Preparation of 2,6-diacetylpyridinebis(2,4,6 trimethyl anil) Iron Dichloride Supported on MAO/silica All operations were conducted under nitrogen unless specified. Silica (256.62 g of grade ES70X supplied by Crosfield), calcined at 200° C. under flowing nitrogen, was placed in a 2L round bottomed flask. Toluene (900 ml) was added to the silica followed by methyl aluminoxane (441 ml, 1.5M in toluene supplied by Witco). The MAO was allowed to react with the silica at room temperature for 10 minutes at which point the temperature was raised to 80° C. and the slurry was mixed occasionally by manually shaking the flask. The temperature was maintained between 80–100° C. for a period of 2 hours.

2,6-diacetylpyridinebis(2,4,6 trimethyl anil) iron dichloride prepared as in Example 9 above (3.48 g) was slurried in toluene (50 ml) and added to the MAO/silica slurry at 80° C. A further aliquot of toluene (20 ml) was used to ensure that all of the Fe complex was transferred to the MAO/silica. The Fe/MAO/silica was then heated at 80° C., with occasional shaking, for 1.5 hours and the solid allowed to settle. The clear supernatant solution was decanted from the flask and the catalyst partially dried under vacuum at 80° C. for 30 minutes and then left at room temperature for 16 hours. Drying of the catalyst was then continued, at 80° C. under vacuum for a further 5 hours, until a dry free flowing powder resulted and no more solvent could be detected coming off the support.

43.4—Pilot Scale Polymerisations (Slurry)

A 93 liter Phillips continuous polymerisation loop reactor was used for the polymerisations. Ethylene, isobutane diluent, hydrogen and the catalyst prepared in Example 1.3 above were metered into the reactor to maintain the reaction conditions as detailed in the Table below. The reactor was operated at a polyethylene throughput of approximately 7.5 kg/hour. Polymer molecular weight was controlled by variation of hydrogen addition rate. Two runs were conducted, one with no separately added alkylaluminium compound as defined as component (3) in the present invention, and one with added TIBA. Other conditions were kept the same except for the hydrogen addition rate, which was reduced with TIBA addition in order to maintain a similar HLMI.

Pilot Scale Conditions

| Reaction conditions: | No TIBA | TIBA added |
|---|---|---|
| Temperature (° C.) | 90 | 90 |
| Pressure (psig) | 600 | 600 |
| Production rate (kg/hr) | 7.4 | 7.3 |
| Ethylene (vol %) | 16.1 | 16.6 |
| Isobutane (litres/hour) | 24 | 24 |
| Hydrogen conc. (vol %) | 0.13 | 0.07 |
| Residence time (hours) | 1.6 | 1.6 |
| TIBA (0.03M/l) ml/hr | 0 | 310 |
| Catalyst Productivity (g/g) | 5310 | 7700 |
| Compounded product: | | |
| HLMI (21.6 kg: g/10 mins) | 4.7 | 4.0 |
| Density (kg/m$^3$) | 959.9 | 959.4 |

The above table clearly shows the significant effect on productivity of adding TIBA.

Example 44

Sluffy Polymerisation Using Varying Amounts of MAO and TMA

This Example shows the effect on activity of varying the amounts of methylalumoxane (MAO) and trimethylaluminium (TMA) employed. The TMA used was as supplied by Aldrich. The MAO was supplied by Aldrich as a 7 wt % solution, and prepared by removing all volatiles in vacuo and washing the residual solid three times in pentane. This was then dried once more in vacuo and stored under nitrogen.

10 44.1—Polymerisation of Ethylene Using 2,6-diacetylpyridinebis(2,6 diisopropyl anil) Iron Dichloride A high-pressure glass bottle equipped with mechanical stirrer, internal cooling loop and internal pressure and temperature monitors was dried at 50° C. under vacuum for 4 hours with frequent flushing by dry nitrogen. A 10 ml stainless steel double-ended injection tube was charged under nitrogen with 5 ml of toluene and 1 μmol of the iron catalyst prepared in Example 1 above. A second similar tube was charged with 5 ml toluene, and appropriate quantities of MAO and TMA (see Table below for amounts).

The toluene/MAO/TMA mixture was the injected with a stream of 200 ml toluene under 2 bar nitrogen back-pressure unto the glass bottle reactor vessel. The reactor was then vented, pressurised with 4 bar ethylene and stirred at 1000 rpm at room temperature. After 15 minutes the iron catalyst/toluene mixture was injected into the reactor under 4 bar ethylene pressure, the reactor venting to provide the pressure differential. The temperature was maintained at 35–40° C. for 15 minutes, and temperature and ethylene flow rate recorded every minute. After 15 minutes the reaction was quenched by the injection of 10 ml methanol. The reactor was vented, and a further 200 ml methanol added. The polymer was collected by filtration, and dried overnight in air.

The experiment was repeated several times with varying quantities of MAO and TMA relative to the amount of iron complex (1 equivalent=1 μmol). The table below shows the activities measured for each run.

Activities Measured for Each Run (g/mmol·h·bar)

|  |  | Equivalents of MAO | | |
|---|---|---|---|---|
|  |  | 200 | 500 | 1000 |
| Equivalents of TMA | 100 | 190 | 450 | 9400 |
|  | 500 | 8170 | 9750 | 9770 |
|  | 1000 | 12600 | 12410 | 13050 |

1000 equivs MAO = 58 mg
1000 equivs TMA = 0.10 ml

44.2—Polymerisation of Ethylene Using 2,6-diacetylpyridinedis(2,6 dimethyl anil) Iron Dichloride Experiment 44.1 was repeated using the iron complex prepared in Example 8 above. Results are shown in the Table below.

Activities Measured for Each Run (g/mmol·h·bar)

|  |  | Equivalents of MAO | | |
|---|---|---|---|---|
|  |  | 200 | 500 | 1000 |
| Equivalents of TMA | 100 | 708 | 2704 | 4000 |
|  | 500 | 9600 | 13160 | 5920 |
|  | 1000 | 12480 | 14670 | 14160 |

1000 equivs MAO = 58 mg
1000 equivs TMA = 0.10 ml

It can be seen from the above tables that even when the total quantity of aluminium (from MAO and TMA combined) in the system is the same, the activity still varies depending on the source of the Al. For example, greater activity is observed with 1000 equivalents of TMA and 500 equivalents of MAO than with 1000 equivalents of MAO and 500 equivalents of TMA.

What is claimed is:

1. A catalyst for the polymerization of olefins comprising
(1) a compound of the formula B

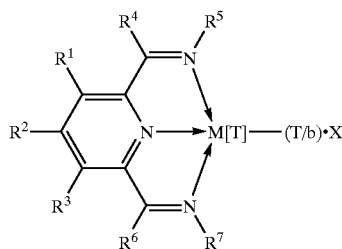

Formula B wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from the group consisting of hydrogen, halogen, hydrocarbyl, substituted hydrocarbyl, heterohydrocarbyl and substituted heterohydrocarbyl; and when any two or more of $R^1$–$R^7$ are hydrocarbyl, substituted hydrocarbyl, heterohydrocarbyl or substituted heterohydrocarbyl, said two or more of $R^1$–$R^7$ can be linked to form one or more cyclic substituents;
(2) an activator which is an alkylalumoxane; and
(3) a compound of the formula $AlR_3$, where each R is independently $C_1$–$C_{12}$ alkyl or halo.

2. The catalyst of claim 1, wherein $R^5$ and $R^7$ are independently selected from the group consisting of substituted or unsubstituted alicyclic groups, substituted or unsubstituted heterocyclic groups, and substituted or unsubstituted aromatic groups.

3. The catalyst of claim 2, wherein $R^5$ and $R^7$ are selected from the group consisting of phenyl, 1-naphthyl, 2-naphthyl, 2-methylphenyl, 2-ethylphenyl, 2,6-diisopropylphenyl, 2,3-diisopropylphenyl, 2,4-diisopropylphenyl, 2-6-di-n-butylphenyl, 2,6-dimethyphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5 dichloro2,6-diethylphenyl, and 2,6,bis (2,6-dimethylphenyl)phenyl, cyclohexyl and pyridinyl.

4. The catalyst of claim 1, wherein the compound (1) has the Formula Z:

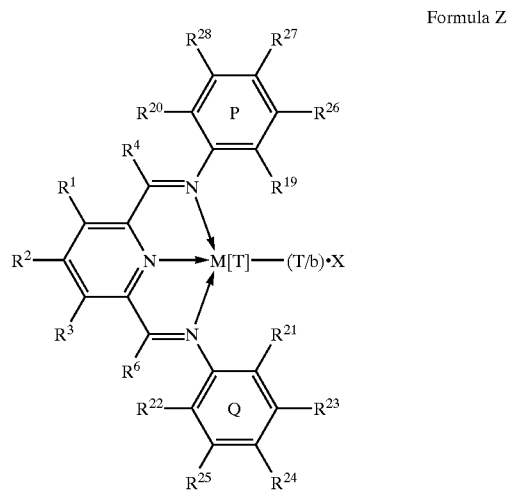

Formula Z wherein $R^{19}$ to $R^{28}$ are independently selected from the group consisting of hydrogen, halogen, hydrocarbyl, substituted hydrocarbyl, heterohydrocarbyl and substituted heterohydrocarbyl; and when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more of $R^1$ to $R^4$, $R^6$ and $R^{19}$ to $R^{28}$ can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of ring systems P and Q form part of a polyaromatic fused-ring system.

5. The catalyst of claim 4, wherein the ring systems P and Q in Formula Z are independently 2,6-hydrocarbylphenyl or fused-ring polyaromatic.

6. The catalyst of claim 5, wherein the ring systems P and Q are independently 1-naphthyl, 2-naphthyl, 1-phenanthrenyl or 8-quinolinyl.

7. The catalyst of claim 4, wherein $R^1$ to $R^4$, $R^6$ and $R^{19}$ to $R^{28}$ are independently selected from the group consisting of hydrogen and $C_1$ to $C_8$ hydrocarbyl.

8. The catalyst of claim 7, wherein $R^1$ to $R^4$, $R^6$ and $R^{19}$ to $R^{28}$ are independently selected from the group consisting of hydrogen, methyl, ethyl, n-propyl, n-butyl, n-hexyl, and n-octyl.

9. The catalyst of claim 1, wherein the compound (1) has the Formula T:

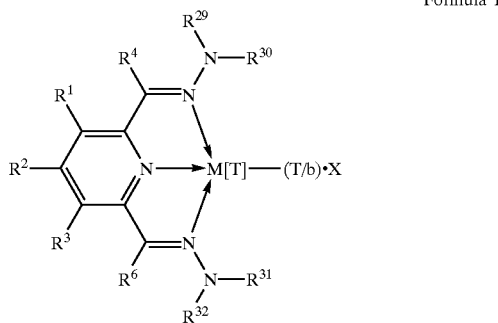

Formula T wherein $R^{29}$ to $R^{32}$ are independently selected from the group consisting of hydrogen, halogen, hydrocarbyl, substituted hydrocarbyl, heterohydrocarbyl and substituted heterohydrocarbyl; and when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more of $R^1$ to $R^4$, $R^6$ and $R^{29}$ to $R^{32}$ can be linked to form one or more cyclic substituents.

10. The catalyst of claim 1, wherein M is Fe[II] or Co[II].

11. The catalyst of claim 1, wherein the atom or group X is halide, hydride, hydrocarbyloxide, carboxylate, hydrocarbyl, substituted hydrocarbyl, heterohydrocarbyl, tosylate, or triflate.

12. The catalyst of claim 11, wherein the halide is chloride or bromide; the hydrocarbyloxide is methoxide, ethoxide, iosppopoxide or phenoxide; the carboxylate is formate, acetate or benzoate; and the hydrocarbyl is methyl, ethyl, propyl, butyl, octyl, decyl, phenyl or benzyl.

13. The catalyst of claim 1, wherein the compound (1) is selected from the group consisting of 2,6-diacetylpyridinebis(2,6-diisopropylanil)FeCl$_2$
2,6-diacetylpyridine(2,6-diisopropylanil)MnCl$_2$
2,6-diacetylpyridine(2,6-diisopropylanil)CoCl$_2$
2,6-diacetylpyridinebis(2-tert.-butylanil)FeCl$_2$
2,6-diacetylpyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,6-dimethylanil)FeCl$_2$
2,6-diacetylpyridinebis(2,4,6 trimethyl anil)FeCl$_2$
2,6-dialdiminepyridinebis(2,6-dimethylanil)FeCl$_2$
2,6-dialdiminepyridinebis(2,6-diethylanil)FeCl$_2$
2,6-dialdiminepyridinebis(2,6-diisopropylanil)FeCl$_2$
2,6-dialdiminepyridinebis(1-naphthil)FeCl$_2$ and
2,6-bis(1,1-diphenylhydrazone)pyridine FeCl$_2$.

14. The catalyst of claim 1, wherein compound (2) is selected from the group consisting of methylalumoxane and modified methylalumoxane.

15. The catalyst of claim 1, wherein compound (3) is selected from the group consisting of trimethylaluminium, triethylaluminium, tri-isobutylaluminium, tri-n-octylaluminium, ethylaluminium dichloride and diethylaluminium choride.

16. The catalyst of claim 1, wherein the ratio of compound (3) to compound (2) is greater than 1:1.

17. The catalyst of claim 16, wherein the ratio of compound (3) to compound (2) is greater than 5:1.

18. The catalyst of claim 17, wherein the ratio of compound (3) to compound (2) is greater than 10:1.

19. The catalyst of claim 1, which is supported on a support material.

20. The catalyst of claim 19, wherein the support is silica, alumina, zirconia, polyethylene, polystyrene, or poly(aminostyrene).

21. The catalyst of claim 19, wherein the support is slica, compound (2) is methyalumoxane and compound (3) is trimethylaluminium or tri-isobutylaluminium.

22. The catalyst of claim 1, further comprising a neutral Lewis base.

23. The catalyst of claim 22, wherein the Lewis base is a tertiary amine or an aromatic ester.

24. A process for the polymerization or copolymerization of 1-olefins comprising contacting an olefin monomer or olefin monomers under polymerization conditions with a polymerization catalyst as defined in claim 1.

25. The process of claim 24, wherein the compound (1) of the catalyst is activated with activator (2) before contact with the monomer or monomers to be polymerized.

26. The process of claim 24, wherein the polymerization conditions are solution phase, slurry phase or gas phase.

27. The process of claim 26, wherein the polymerization is conducted in slurry phase in an autoclave or continuous loop reactor.

28. The process of claim 26, wherein the polymerization is conducted in slurry phase, and compound (3) is tri-isobutylaluminium or trimethylaluminium.

29. The process of claim 26, wherein the polymerizaiton is conducted under gas phase fluidized bed conditions.

30. The process of claim 29, wherein the polymerization is conducted at a pressure of from 10 to 100 bars and at a temperature of from 50 to 120° C.

31. The process of claim 26, wherein the polymerization is conducted in gas phase and compound (3) is trimethylaluminium.

* * * * *